United States Patent
Shindo

(10) Patent No.: US 12,336,778 B2
(45) Date of Patent: Jun. 24, 2025

(54) SURGICAL TOOL

(71) Applicant: RIVERFIELD INC., Tokyo (JP)

(72) Inventor: Koki Shindo, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 875 days.

(21) Appl. No.: 17/438,205

(22) PCT Filed: Mar. 10, 2020

(86) PCT No.: PCT/JP2020/010395
§ 371 (c)(1),
(2) Date: Sep. 10, 2021

(87) PCT Pub. No.: WO2020/184589
PCT Pub. Date: Sep. 17, 2020

(65) Prior Publication Data
US 2022/0211456 A1 Jul. 7, 2022

(30) Foreign Application Priority Data

Mar. 13, 2019 (JP) ................................. 2019-045601

(51) Int. Cl.
*A61B 34/37* (2016.01)
*A61B 17/00* (2006.01)
(Continued)

(52) U.S. Cl.
CPC .............. *A61B 34/37* (2016.02); *A61B 17/28* (2013.01); *A61B 34/35* (2016.02); *A61B 34/71* (2016.02);
(Continued)

(58) Field of Classification Search
CPC .......... A61B 17/28; A61B 34/35; A61B 34/71
See application file for complete search history.

(56) References Cited

U.S. PATENT DOCUMENTS

| 4,187,826 A | 2/1980 | Killian |
| 4,338,910 A | 7/1982 | Darlington |

(Continued)

FOREIGN PATENT DOCUMENTS

| CN | 105899158 A | 8/2016 |
| CN | 105979901 A | 9/2016 |

(Continued)

OTHER PUBLICATIONS

Extended European Search Report dated May 25, 2022 in European Application No. 20769716.0.

(Continued)

*Primary Examiner* — Erin McGrath
(74) *Attorney, Agent, or Firm* — Sughrue Mion, PLLC

(57) ABSTRACT

In a surgical tool, a cord-shaped element transmits a movement of a driven portion to a working portion. A rotor has a circumferential surface around which the cord-shaped element extending from the driven portion to the working portion is wound. A first and a second supporting portion support the rotor such that the rotor is movable in relation to one or both of the driven portion and the working portion. A rotational shaft includes a first end securable to a first supporting portion, and supports the rotor such that the rotor is rotatable about a rotational axis thereof. A securing portion is arranged between a second end of the rotational shaft and the second supporting portion. A position of the securing portion relative to the rotational shaft is changeable in a rotational axis direction. The securing portion is securable to the second supporting portion.

20 Claims, 7 Drawing Sheets

(51) Int. Cl.
*A61B 17/28* (2006.01)
*A61B 34/00* (2016.01)
*A61B 34/35* (2016.01)
*B25J 15/08* (2006.01)

(52) U.S. Cl.
CPC ..... *B25J 15/08* (2013.01); *A61B 2017/00367* (2013.01); *A61B 2017/00477* (2013.01); *A61B 2034/715* (2016.02)

(56) References Cited

U.S. PATENT DOCUMENTS

| | | |
|---|---|---|
| 2007/0088340 A1 | 4/2007 | Brock et al. |
| 2007/0137372 A1 | 6/2007 | Devengenzo et al. |
| 2010/0198253 A1 | 8/2010 | Jinno et al. |
| 2011/0313405 A1 | 12/2011 | Anderson et al. |
| 2014/0249545 A1 | 9/2014 | Hyodo et al. |
| 2015/0032125 A1 | 1/2015 | Jeong et al. |
| 2016/0317236 A1 | 11/2016 | Hyodo et al. |
| 2017/0105805 A1 | 4/2017 | Hasegawa et al. |
| 2018/0104012 A1 | 4/2018 | Wixey et al. |
| 2018/0125595 A1 | 5/2018 | Yoshii et al. |
| 2019/0223960 A1 | 7/2019 | Chaplin et al. |

FOREIGN PATENT DOCUMENTS

| | | | |
|---|---|---|---|
| CN | 106470632 | A | 3/2017 |
| CN | 107848120 | A | 3/2018 |
| CN | 1083546668 | A | 8/2018 |
| JP | 4938753 | B2 | 5/2012 |
| JP | 2013-103074 | A | 5/2013 |
| JP | 2014-502189 | A | 1/2014 |
| JP | 2019-505260 | A | 2/2019 |
| WO | 03/001986 | A2 | 1/2003 |
| WO | 2015/122944 | A1 | 8/2015 |
| WO | 2017/209695 | A1 | 12/2017 |
| WO | 2018/094191 | A1 | 5/2018 |
| WO | 2018/224826 | A1 | 12/2018 |

OTHER PUBLICATIONS

Extended European Search Report dated May 27, 2022 in European Application No. 20770814.0.
International Search Report issued May 19, 2020 in International Application No. PCT/JP2020/010394.
International Preliminary Report on Patentability issued Aug. 25, 2021 in International Application No. PCT/JP2020/010394.
International Preliminary Report on Patentability issued Aug. 25, 2021 in International Application No. PCT/JP2020/010395.
Office Action dated Feb. 8, 2022 from the China National Intellectual Property Administration in CN Application No. 202080020695.3.
International Search Report for PCT/JP2020/010395, dated May 19, 2020.
Office Action dated Sep. 1, 2022 from the China National Intellectual Property Administration in CN Application No. 202080020695.3.
Notification of Reasons for Refusal dated Jan. 17, 2023 from the Chinese Patent Office in Application No. 202080020695.3.

SURGICAL TOOL

CROSS-REFERENCE TO RELATED APPLICATION

This application is a National Stage of International Application No. PCT/JP2020/010395 filed Mar. 10, 2020, claiming priority based on Japanese Patent Application No. 2019-045601 filed on Mar. 13, 2019 with the Japan Patent Office, the entire contents of each of which being herein incorporated by reference in their entireties.

TECHNICAL FIELD

The present disclosure relates to a surgical tool.

BACKGROUND ART

In regard to master-slave type surgical robots, there have been demands for a technique to transmit external forces acting on robot forceps, which are a type of surgical tool, to operators who operate the robots in isolated places in order to improve safety and shorten the time for doctors to learn the operation. The external forces to be transmitted to the operators are estimated based on information such as the position of actuators and driving forces.

Known methods for driving surgical tools of robots include a method in which a driving force generated by a driving source, such as an actuator, is transmitted to a surgical tool through a wire to drive the surgical tool (see, for example, Patent Document 1). The wire is arranged between the driving source and the surgical tool, and the tension thereof is adjusted to within a specified range.

PRIOR ART DOCUMENT

Patent Document

Patent Document 1: Japanese Patent No. 4938753

SUMMARY OF THE INVENTION

Problems to be Solved by the Invention

In the technique described in Patent Document 1, part of the wire is wound around a columnar or cylindrical adjusting member. The tension of the wire is adjusted by controlling a torque that is a force applied in the direction to reel in the wire on the adjusting member.

It is difficult, however, to make fine adjustment of the wire in the method in which the torque of the adjusting member is controlled to adjust the tension of the wire. It is also difficult to maintain the adjusted tension and fix the tension at the adjusted tension.

The tension of the wire is considered to influence the magnitude of the frictional force generated when the driving force is transmitted to the surgical tool. If more than one wires are provided, the tensions of the wires are different, and thus likely to cause variations in tension. That is, the frictional force generated when the surgical tool is driven is different from one wire to another, for example, different for each movement of the surgical tool. On the other hand, with regard to external force estimation for transmitting the external force acting on the surgical tool, the accuracy of the external force estimation tends to decrease due to changes in the frictional forces generated when the external force is transmitted.

It is desirable that one aspect of the present disclosure provides a surgical tool that can enhance the accuracy of the external force estimation.

Means for Solving the Problems

The present disclosure provides the following means.

One aspect of the present disclosure provides a surgical tool comprising a driven portion, a cord-shaped element, a rotor, a first and a second supporting portion, a rotational shaft, and a securing portion. To the driven portion, a driving force is transmitted from an external portion. The cord-shaped element transmits a movement of the driven portion to a working portion. The rotor has a circumferential surface around which the cord-shaped element extending from the driven portion to the working portion is wound. The first and second supporting portions are arranged such that the rotor is interposed therebetween, and support the rotor such that the rotor is movable in an approaching and separating manner in relation to at least one of the driven portion and the working portion. The rotational shaft includes a first end securable to the first supporting portion, and supports the rotor such that the rotor is rotatable about a rotational axis thereof. The securing portion is arranged between a second end of the rotational shaft and the second supporting portion. A position of the securing portion relative to the rotational shaft is changeable in a rotational axis direction. The securing portion is securable to the second supporting portion.

In the surgical tool according to the present disclosure, the arrangement position of the rotor can be changed in the approaching and separating manner in relation to at least one of the driven portion and the working portion, and thereby the tension of the cord-shaped element can be adjusted. In comparison with, for example, the tension adjustment method described in Patent Document 1, it is easy to finely adjust the tension and to maintain the adjusted tension. Moreover, it is possible to reduce the variation in tension to stabilize the tension. Thus, the frictional force acting between the driven portion and the working portion is also stabilized. This facilitates improvement in accuracy of external force estimation.

Furthermore, the rotational shaft and the securing portion are configured such that the relative positions thereof in the rotational axis direction can be changed. Thus, the rotation of the rotor is less likely to be inhibited. In the case, for example, where the rotational shaft is secured to the first supporting portion and the securing portion is secured to the second supporting portion, which is the other supporting portion, the length of the combination of the rotational shaft and the securing portion is adjusted by changing the relative positions even when the length of the combination is different from the distance between the first and second supporting portions. Accordingly, the influence of the securing does not easily reach the rotor supported by the rotational shaft, and the rotation is less likely to be inhibited.

In the case where two or more rotors are provided, it is easy to change the arrangement position of each of the rotors in the approaching and separating manner. In other words, even after fixing the arrangement position of one rotor, the arrangement positions of other rotors can be easily changed in the approaching and separating manner.

In the case, for example, where there are no securing portions and only the rotational shafts are provided, in response to the arrangement position of one of the rotors being fixed, each end of the rotational shaft of the one rotor comes into contact with the first supporting portion or the second supporting portion. At this time, the first and second supporting portions come close to each other and the distance therebetween becomes equal to the length of the rotational shaft. That is, each end of the rotational shafts of the other rotors also comes into contact with the first supporting portion or the second supporting portion. Then, despite an attempt to change the arrangement positions of the other rotors in the approaching and separating manner, the ends of the rotational shafts of the other rotors cannot be easily moved in the approaching and separating manner since the frictional force acting on the surfaces in contact with the first and second supporting portions tends to large.

In contrast, in the case where the relative positions of the rotational shafts and the securing portions can be changed, the first and second supporting portions do not come close to each other even after fixing the arrangement position of one rotor. That is, the frictional force acting on the contacting surfaces between the rotational shafts of the other rotors and the supporting portion, and the contacting surfaces between the securing portions and the supporting portion is less likely to be large. Accordingly, even after fixing the arrangement position of one rotor, it is easy to change the arrangement positions of other rotors in the approaching and separating manner.

Furthermore, the length of the combination is adjusted by changing the relative positions. Thus, a load is less likely to be imposed on the first and second supporting portions. In the case, for example, where the first and second supporting portions are plate-shaped members extending in a direction intersecting the rotational shafts, the load may cause deformation or breakage of the first and second supporting portions. Even in such a case, it is easy to inhibit deformation and breakage of the first and second supporting portions since the load is less likely to be imposed thereon.

In one aspect of the present disclosure, the first supporting portion and the second supporting portion may comprise an elongated hole extending in an approaching and separating direction of the rotor. A stator inserted in the elongated hole may be provided to facilitate pressing of the rotational shaft and the securing portion respectively against the first supporting portion and the second supporting portion.

Pressing the rotational shaft against the first supporting portion and pressing the securing portion against the second supporting portion using the elongated hole and the stator in this way enables fixation of the arrangement position of the rotor in relation to at least one of the driven portion and the working portion. Increasing the pressing force enables more reliable fixation of the arrangement position, and reducing the pressing force facilitates changes in the arrangement position.

In one aspect of the present disclosure, one of the rotational shaft and the securing portion may comprise a projection extending in the rotational axis direction that is a direction of the rotational axis, and another may comprise a recess that engages with the projection.

Use of the projection extending in the rotational axis direction and the recess engaged with the projection as described above allows changes in the position of the rotational shaft relative to the securing portion in the rotational axis direction. Moreover, it is possible to maintain the relative position in the direction intersecting the rotational axis direction.

In one aspect of the present disclosure, the driven portion may be moved linearly in a reciprocating manner by the driving force transmitted. The rotor may be arranged such that the driven portion is interposed between the rotor and the working portion. Of ends of the cord-shaped element wound around the rotor, a first end of the cord-shaped element may be arranged to extend toward the driven portion, and a second end of the cord-shaped element may be arranged to extend toward the working portion.

Arrangement of the driven portion between the rotor and the working portion and transmission of the reciprocating movement of the driven portion to the working portion through the cord-shaped element wound around the rotor facilitate adjustment of the tension of the cord-shaped element.

Effects of the Invention

In the surgical tool according to the present disclosure, the arrangement position of the rotor can be changed in the approaching and separating manner in relation to at least one of the driven portion and the working portion, and the rotational shaft and the securing portion are configured such that the relative positions thereof in the rotational axis direction can be changed. Accordingly, the surgical tool achieves an effect of enhancing the accuracy of the external force estimation.

EXPLANATION OF REFERENCE NUMERALS

1 . . . surgical tool, 3 . . . motive power transmitter (external portion), 12 . . . forceps (working portion), 21 . . . first housing portion (supporting portion), 22 . . . second housing portion (supporting portion), 23 . . . elongated hole for pulley (elongated hole), 31 . . . drive element (driven portion), 35 . . . wire (cord-shaped element), 41 . . . pulley (rotor), 46 . . . pulley's rotational shaft (rotational shaft), 49 . . . leading end (projection), 51 . . . securing block (securing portion), 52 . . . recess, 56 . . . securing screw (stator)

MODE FOR CARRYING OUT THE INVENTION

Figure 1:
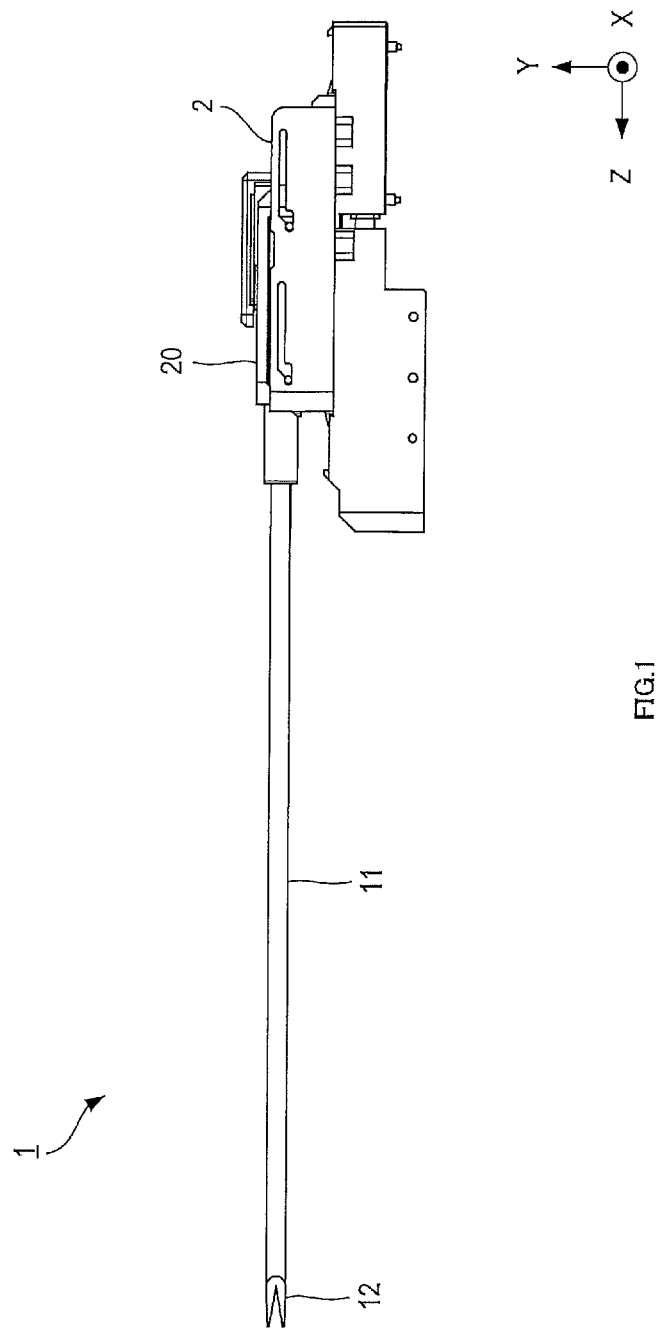
FIG. 1 is a diagram illustrating a configuration of a surgical tool according to one embodiment of the present disclosure.

A surgical tool 1 according to one embodiment of the present disclosure will be described with reference to FIGS. 1 to 7. The surgical tool 1 of the present embodiment is applied to a master-slave type surgical robot. The surgical tool 1 of the present embodiment is used for surgery. As shown in FIG. 1, the surgical tool 1 comprises a shaft 11 with forceps 12 arranged at its leading end, and a housing 20 to be attached to the surgical robot. The forceps 12 correspond to the working portion.

The shaft 11 is a rod-shaped member extending from the housing 20. In the present embodiment, the shaft 11 is a rod-shaped member extending along the Z-axis direction. The forceps 12, which are the working portion, are provided at the leading end of the shaft 11 that is the end remote from the housing 20. Inside the shaft 11, a space is provided extending from the housing 20 toward the forceps 12. A wire 35, which will be described later, can be arranged in this space.

Hereinafter, the end of the shaft 11 remote from the housing 20 is the end on the positive side of the Z axis, and the direction from the housing 20 toward the forceps 12 is the positive direction of the Z-axis.

Figure 2:
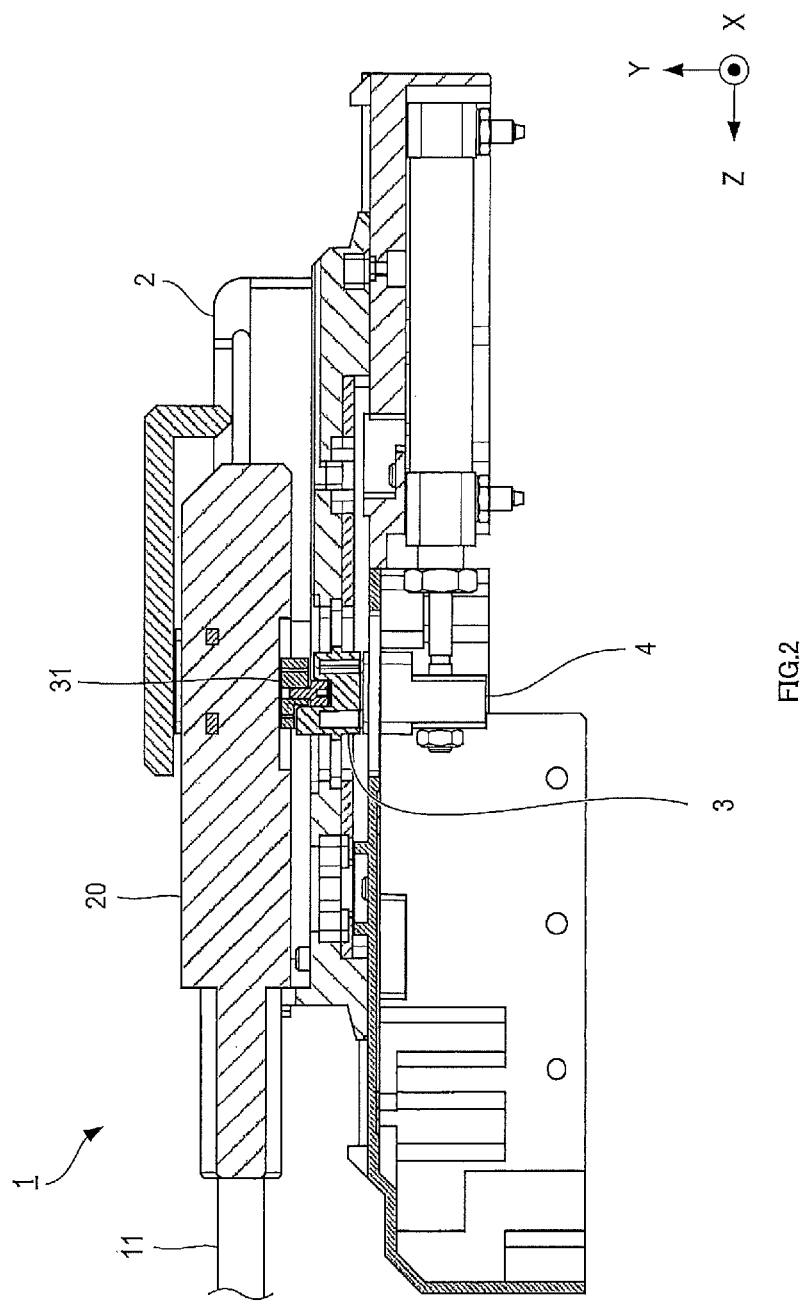
FIG. 2 is a partial sectional view illustrating a state of the surgical tool in FIG. 1 engaged with an adapter.

As shown in FIG. 2, the housing 20 is attachable to and detachable from an adapter 2 of the surgical robot. To the housing 20, a driving force that drives the forceps 12 is transmitted from a power device 4 via a motive power transmitter 3 of the adapter 2. The motive power transmitter 3 corresponds to the external portion.

Figure 3:
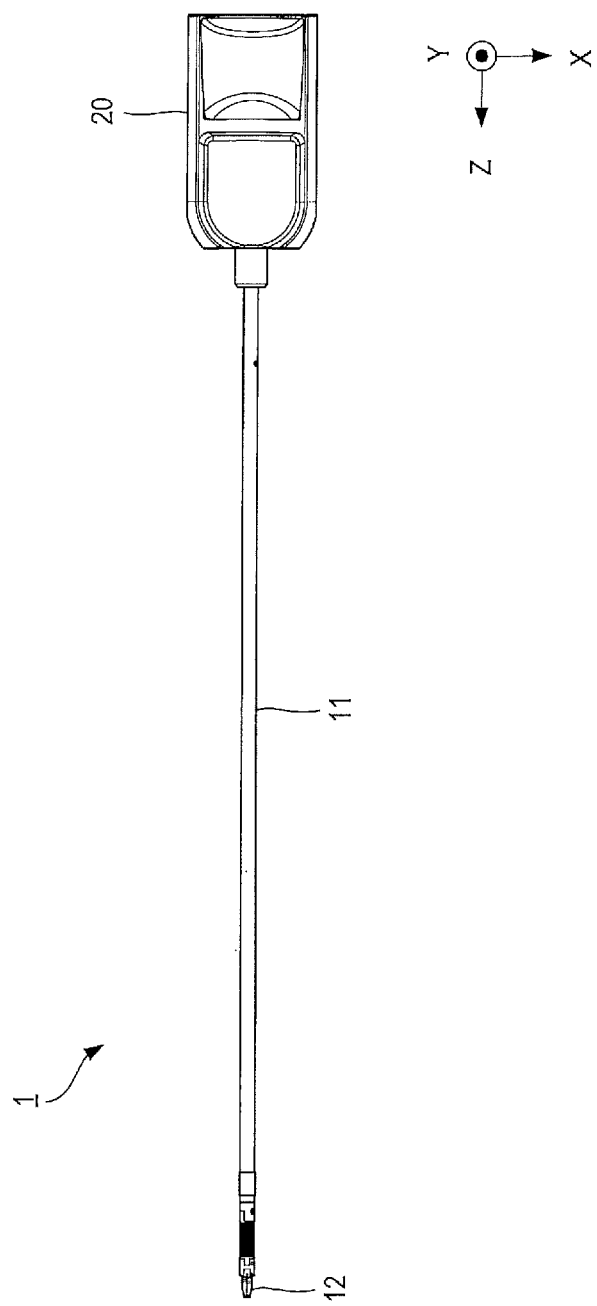
FIG. 3 is a perspective view illustrating arrangement positions of a first housing portion and a second housing portion of the surgical tool in FIG. 1.
Figure 4:
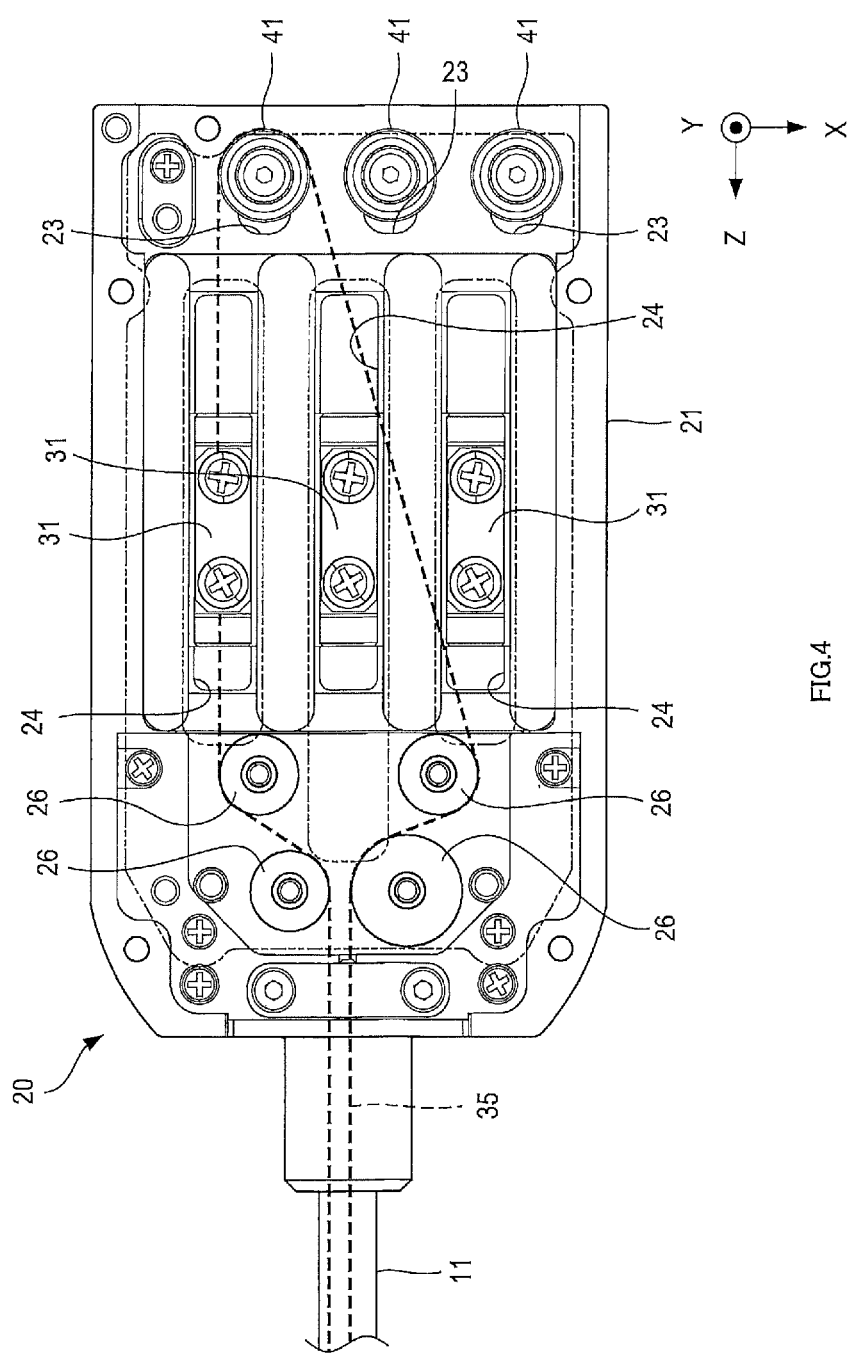
FIG. 4 is a top view illustrating a configuration inside of a housing in FIG. 1.
Figure 5:
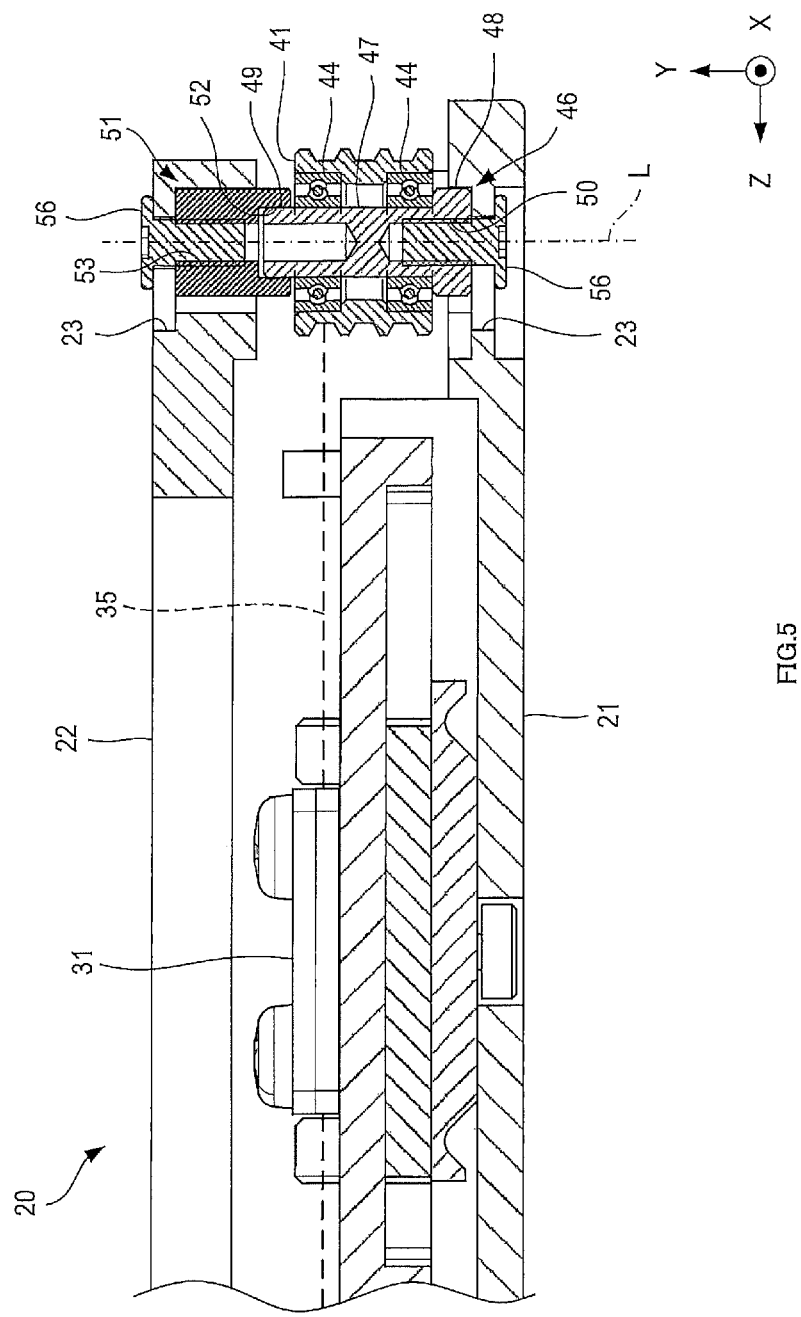
FIG. 5 is a partial sectional view illustrating the configuration inside of the housing in FIG. 1.

As shown in FIGS. 3 to 5, the housing 20 comprises a first housing portion 21, a second housing portion 22, drive elements 31, the wire 35, pulleys 41, pulleys' rotational shafts 46, securing blocks 51, and securing screws 56.

The first and second housing portions 21, 22 respectively correspond to the first and second supporting portions. The drive elements 31, the wire 35, the pulleys 41, the pulleys' rotational shafts 46, the securing blocks 51, and the securing screws 56 respectively correspond to the driven portion, the cord-shaped element, the rotor, the rotational shaft, the securing portion, and the stator.

As shown in FIGS. 4 and 5, the first and second housing portions 21, 22 are plate-shaped members that form at least part of the body of the housing 20. In the present embodiment, the first housing portion 21 is arranged on the surface of the housing 20 facing the adapter 2, and the second housing portion 22 is arranged on the surface of the housing 20 remote from the adapter 2. Moreover, the first and second housing portions 21, 22 are arranged parallel to the X-Z plane.

In the housing 20, the surface facing the adapter 2 is the surface on the negative side of the Y-axis, and the surface remote from the adapter 2 is the surface on the positive side of the Y-axis.

As shown in FIGS. 4 and 5, at least the wire 35, guide pulleys 26, the pulleys 41, the pulleys' rotational shafts 46, and the securing blocks 51 are arranged between the first and second housing portions 21, 22.

Elongated holes 23 for pulleys that are used for arranging the pulleys 41 are provided in the areas of the first and second housing portions 21, 22 located near the ends remote from the shaft 11, that is, in the areas near the ends on the negative side of the Z-axis.

Each elongated hole 23 for pulley is a through-hole extending to the positive side of the Z-axis, which is toward the shaft 11 in the first and second housing portions 21, 22. In other words, each elongated hole 23 for pulley is an elongated hole extending along the Z-axis direction. In the present embodiment, three elongated holes 23 for pulleys are arranged side by side at intervals in the X-axis direction. The number of the elongated holes 23 for pulleys to provide is not limited to three, and may be more or less than three.

The first housing portion 21 is provided with elongated holes 24 for driving in which the drive elements 31 are arranged. Each of the elongated holes 24 for driving allows the movement of the drive element 31 in the direction along the first housing portion 21, and restricts the movement in the direction away from the first housing portion 21, that is, in the Y-axis direction.

The elongated holes 24 for driving are provided near the shaft 11 as compared with the elongated holes 23 for pulleys in the first housing portion 21. For example, the elongated holes 24 for driving are provided in the central area of the first housing portion 21 in the Z-axis direction.

Each of the elongated holes 24 for driving is a through-hole linearly extending toward the shaft 11, that is, to the positive side of the Z-axis. In other words, each of the elongated holes 24 for driving is an elongated hole extending along the Z-axis direction. In the present embodiment, the three elongated holes 24 for driving are arranged side by side at intervals in the X-axis direction. The number of the elongated holes 24 for driving to provide may correspond to the number of the elongated holes 23 for pulleys, may be more than three, or may be less than three.

In the present embodiment, the three elongated holes 24 for driving are equal in length in the Z-axis direction. The lengths of the three elongated holes 24 for driving in the Z-axis direction may be equal as mentioned above, or may be different.

The guide pulleys 26 guide the wire 35, extending from the drive elements 31 to the shaft 11, to the internal space of the shaft 11. More specifically, the guide pulleys 26 guide the wire 35, extending from the drive elements 31 arranged on the positive side or the negative side of the shaft 11 in the X-axis direction away from the shaft 11, to the shaft 11.

As shown in FIGS. 4 and 5, the guide pulleys 26 are arranged between the first and second housing portions 21, 22 and adjacent to the shaft 11, that is, in the end area on the positive side of the Z-axis. In other words, the guide pulleys 26 are arranged in the space between the first and second housing portions 21, 22 and between the elongated holes 24 for driving and the shaft 11.

The guide pulleys 26 are attached to at least one of the first and second housing portions 21, 22, and are rotatable about the axes extending in the Y-axis direction. The shape and configuration of the guide pulleys 26 are not particularly limited.

As shown in FIGS. 4 and 5, in response to transmission of the driving force from the motive power transmitter 3 of the adapter 2, each of the drive elements 31 sends the transmitted driving force to the wire 35. Each of the drive elements 31 reciprocates along the elongated hole 24 for driving due to the driving force transmitted from the motive power transmitter 3.

On the surface of each drive element 31 facing the elongated hole 24 for driving, an uneven shape is formed to allow a relative movement of the drive element 31 along the first housing portion 21 and to restrict a movement of the drive element 31 in a direction to be disengaged from the first housing portion 21. Each of the elongated holes 24 for driving is provided with an uneven shape formed to be joined with the uneven shape of the drive element 31. The shape of this uneven shape is not particularly limited.

A further uneven shape used for transmitting the driving force is formed in the area of each drive element 31 facing the motive power transmitter 3. This uneven shape formed on each drive element 31 is also a shape that allows the drive element 31 and the motive power transmitter 3 to be engaged and separated in the Y-axis direction. The shape of this uneven shape is not particularly limited.

The wire 35 transmits the driving force, sent to the drive elements 31, to the forceps 12. In other words, the wire 35 transmits the movements of the drive elements 31 to the forceps 12. The material and shape of the wire 35 are not particularly limited.

The wire 35 extending from the drive elements 31 in the negative direction of the Z-axis is wound around the pulleys 41. The wire 35, after being wound around the pulleys 41, extends in the positive direction of the Z-axis to be guided into the shaft 11. Of the ends of the wire 35, the end extending toward the drive elements 31 corresponds to the first end of the cord-shaped element, and the end arranged to extend toward the shaft 11 corresponds to the second end of the cord-shaped element.

The wire 35 extending from the drive elements 31 in the positive direction of the Z-axis is wound around the guide pulleys 26 and guided into the shaft 11 in the case, for example, where the drive elements 31 are arranged on the positive side of the shaft 11 in the X-axis direction away from the shaft 11.

The wire 35 guided into the shaft 11 transmits the driving force to the forceps 12. The configuration for transmitting the driving force may be, for example, a configuration in which each end of the wire 35 guided into the shaft 11 is attached to the forceps 12, or each end of the wire 35 is connected to the other end to form a loop and wound around a pulley provided to the forceps 12.

The pulleys 41 are members formed in a cylindrical shape having a circumferential surface around which the wire 35 is wound, and change the direction of the wire 35 extending from the drive elements 31 in the negative direction of the Z-axis to the positive direction of the Z-axis.

Each of the pulleys 41 is placed in the elongated hole 23 for pulley using the pulley's rotational shaft 46, the securing block 51, and the securing screws 56. In other words, each of the pulleys 41 is arranged at a position where the drive element 31 is interposed between the shaft 11, provided with the forceps 12, and the pulley 41.

Each of the pulleys 41 is formed in a cylindrical shape. The cylindrical pulley 41 is formed having a length in the direction of its central axis smaller than the distance between the first and second housing portions 21, 22. In other words, the cylindrical pulley 41 is formed having a height in the Y-axis direction smaller than the distance between the first and second housing portions 21, 22.

The internal space of the cylindrical pulley 41 is a space where the pulley's rotational shaft 46 is arranged, and bearings 44 that support the pulley 41 such that the pulley 41 is rotatable about the rotational axis L are arranged between the pulley 41 and the pulley's rotational shaft 46. The central axis of the pulley 41 and the rotational axis L coincide with each other.

Figure 6A:
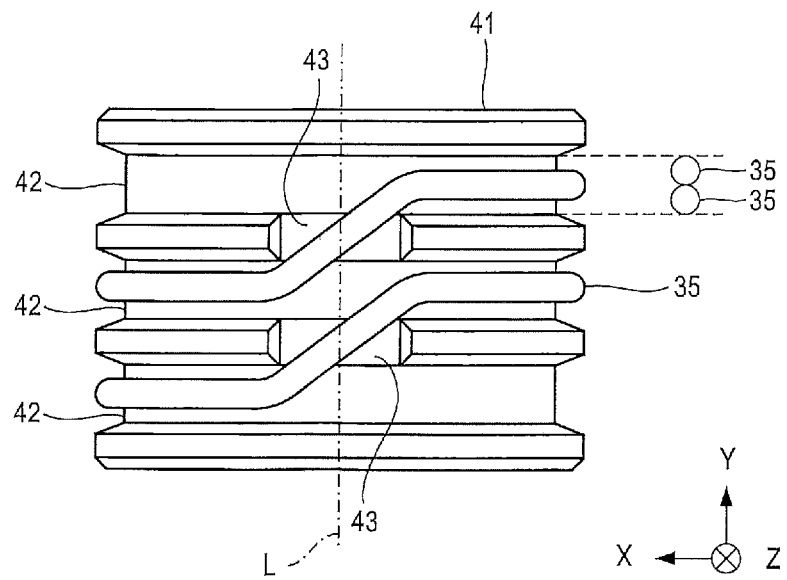
FIG. 6A is a diagram illustrating configurations of grooves and cut-out portions formed on a pulley.

As shown in FIG. 6A, the circumferential surface of the cylindrical pulley 41 is provided with three annular grooves 42 next to each other in an equidistant manner in the direction of the central axis of the pulley 41, that is, along the Y-axis direction. In the present embodiment, each of the three grooves 42 has a width equal to the length of two wires 35 arranged side by side. The width of each of the three grooves 42 may be larger or smaller than the length of the two wires 35 arranged side by side.

Moreover, each of the pulleys 41 is provided with two cut-out portions 43 connecting the adjacent grooves 42. Each of the two cut-out portions 43 is formed by scraping off part of a ridge-shaped protrusion that partitions the adjacent grooves 42, and have a width in which the wire 35 can be arranged from one groove 42 to another groove 42. In the present embodiment, the two cut-out portions 43 are provided side by side in the same phase of the circumferential surface of the pulley 41. The two cut-out portions 43 may be provided side by side in the same phase, or may be provided in different phases.

As shown in FIG. 5, the pulleys' rotational shafts 46 are cylindrical or columnar members that support the pulleys 41 such that pulleys 41 are rotatable. Each of the pulleys' rotational shafts 46 comprises an insertion portion 47 inserted into the bearings 44 arranged in the internal space of each pulley 41, and an enlarged-diameter portion 48 provided at one end of the insertion portion 47. A leading end 49 of the insertion portion 47 is inserted into a recess 52 of the securing block 51, which will be described below. The leading end 49 of the insertion portion 47 corresponds to the projection.

The enlarged-diameter portion 48 has a shape with a diameter larger than the inner diameter of the bearings 44 into which the insertion portion 47 is inserted. Each of the pulleys' rotational shafts 46 has a length such that the end of the insertion portion 47 and the end of the enlarged-diameter portion 48 protrude from the corresponding pulley 41 when the insertion portion 47 is inserted into the bearings 44 and the enlarged-diameter portion 48 is in contact with the bearing 44.

Each of the pulleys' rotational shafts 46 is provided, on the end surface that is where the enlarged-diameter portion 48 is located, with a screw hole 50 with which the securing screw 56 threadedly engages. The screw holes 50 are provided on the central axes of the cylindrical or columnar pulleys' rotational shafts 46. The screw holes 50 may be holes penetrating the pulleys' rotational shafts 46, or holes with closed ends.

The securing blocks 51 are cylindrical or columnar members that support the pulleys 41 together with the pulleys' rotational shafts 46. Each securing block 51 is provided, at the end thereof adjacent to the pulley's rotational shaft 46, with the recess 52 into which the leading end 49 of the insertion portion 47 is inserted, and, at the opposite end thereof, a screw hole 53 with which the securing screw 56 threadedly engages.

In the present embodiment, the securing block 51 is provided with the recess 52, and the leading end 49 of the insertion portion 47 is inserted into the recess 52; the configuration, however, may be such that the insertion portion 47 is provided with a recess, and a projection that the securing block 51 is provided is inserted into the recess.

Each of the securing blocks 51 is arranged between the leading end 49 of the pulley's rotational shaft 46 and the second housing portion 22. The securing blocks 51 are movable in the Z-axis direction relative to the second housing portion 22 and are securable to the second housing portion 22. The position of each of the securing blocks 51 relative to the pulley's rotational shaft 46 can be changed along the Y-axis direction, and the movements thereof relative to the pulley's rotational shaft 46 in the X-axis and Z-axis directions are restricted.

As shown in FIG. 5, each of the securing screws 56 is a male screw that is inserted into the elongated hole 23 for pulley and threadedly engages with the pulley's rotational shaft 46 or the securing block 51. The securing screw 56 threadedly engaged with the screw hole 50 of the pulley's rotational shaft 46 holds the first housing portion 21 together with the pulleys' rotational shafts 46. Moreover, the securing screw 56 threadedly engaged with the screw hole 50 of the pulley's rotational shaft 46 presses the pulley's rotational shaft 46 against the first housing portion 21 to secure the pulley's rotational shaft 46. The securing screw 56 threadedly engaged with the screw hole 53 of the securing block 51 holds the second housing portion 22 together with the securing block 51. The securing screw 56 threadedly engaged with the screw hole 53 of the securing block 51 presses the securing block 51 against the second housing portion 22 to secure the securing block 51.

Next, the operation of the surgical tool 1 having the above configuration will be described.

As shown in FIG. 2, the driving force that drives the forceps 12 of the surgical tool 1 is transmitted from the power device 4 to the drive elements 31 via the motive power transmitter 3 of the adapter 2. As shown in FIGS. 2 and 4, the drive elements 31 reciprocate relative to the housing 20 along the Z-axis direction along the elongated holes 24 for driving.

The movement of each of the drive elements 31 is transmitted to the wire 35. The wire 35 reciprocates along its extending direction. The wire 35 extending from the drive elements 31 toward the forceps 12, that is, to the positive side of the Z-axis direction reciprocates in the direction guided by the guide pulleys 26. The wire 35 extending from the drive elements 31 to the side where the pulleys 41 are arranged, that is, to the negative side of the Z-axis direction reciprocates along the direction guided by the pulleys 41 and the guide pulleys 26.

The wire 35 extends through the internal space of the shaft 11 to the forceps 12, and the reciprocating movement of the wire 35 is transmitted to the forceps 12. The forceps 12 open/close based on the reciprocating movement of the wire 35. Although the forceps 12 open/close based on the reciprocating movement of the wire 35 in the present embodiment, the forceps 12 may also make other movements, such as bending, in order to change the direction of the forceps 12.

Next, a method for tensioning the wire 35, that is, adjusting the tension of the wire 35 will be described with reference to FIGS. 4 and 5. First, tensioning of the wire 35 is performed by changing the positions of the pulleys 41 relative to the housing 20. Specifically, the tension is adjusted by moving the pulleys 41 along the elongated holes 23 for pulleys along the Z-axis direction. For example, the tension is increased as the pulleys 41 are moved in the direction away from the shaft 11, that is, in the negative direction of the Z-axis, and the tension is reduced as the pulleys 41 are moved in the direction approaching the shaft 11, that is, in the positive direction of the Z-axis.

When the pulleys 41 are moved along the elongated holes 23 for pulleys, the securing screws 56 threadedly engaged with the pulleys' rotational shafts 46 are loosened, and the securing screws 56 threadedly engaged with the securing blocks 51 are loosened. In other words, the force pressing the pulleys' rotational shafts 46 against the first housing portion 21 is reduced, and the force pressing the securing blocks 51 against the second housing portion 22 is reduced.

As a result, the pulleys' rotational shafts 46 and the securing blocks 51 can come relatively close to each other in the Y-axis direction. Accordingly, gaps can be formed between the pulleys' rotational shafts 46 and the first housing portion 21, and between the securing blocks 51 and the second housing portion 22.

Subsequently, the pulleys 41 are moved in relation to each other to positions where the tension of the wire 35 is at a desired value. When the relative positions of the pulleys 41 are determined, the securing screws 56 threadedly engaged with the pulleys' rotational shafts 46 are tightened, and the securing screws 56 threadedly engaged with the securing blocks 51 are tightened. At this time, the pulleys' rotational shafts 46 and the securing blocks 51 are separated in a relative manner in the Y-axis direction.

In other words, the force pressing the pulleys' rotational shafts 46 against the first housing portion 21 is increased, and the force pressing the securing blocks 51 against the second housing portion 22 is increased. This increases the frictional force between the pulleys' rotational shafts 46 and the first housing portion 21, and between the securing blocks 51 and the second housing portion 22. That is, the arrangement positions of the pulleys 41 are fixed.

Next, the winding of the wire 35 around the pulley 41 will be described with reference to FIGS. 6A to 7B. In the case, for example, where the wire 35 guided into the shaft 11 is arranged side by side in the Y-axis direction as shown in FIG. 6B, the wire 35 is wound around the pulley 41 as shown in FIG. 6A.

Specifically, the wire 35 extending from the drive elements 31 or the shaft 11 is wound in the groove 42 on the positive side or the negative side of the Z-axis direction of the pulley 41. In the cut-out portion 43, the wire 35 wound in the groove 42 is led to the groove 42 provided in the middle of each pulley 41, and wound in the middle groove 42. Further, the wire 35 is wound through the cut-out portion 43 in the groove 42 on the negative side or the positive side of the Z-axis direction of the pulley 41, and then extends to the shaft 11 or the drive elements 31.

Figure 6B:
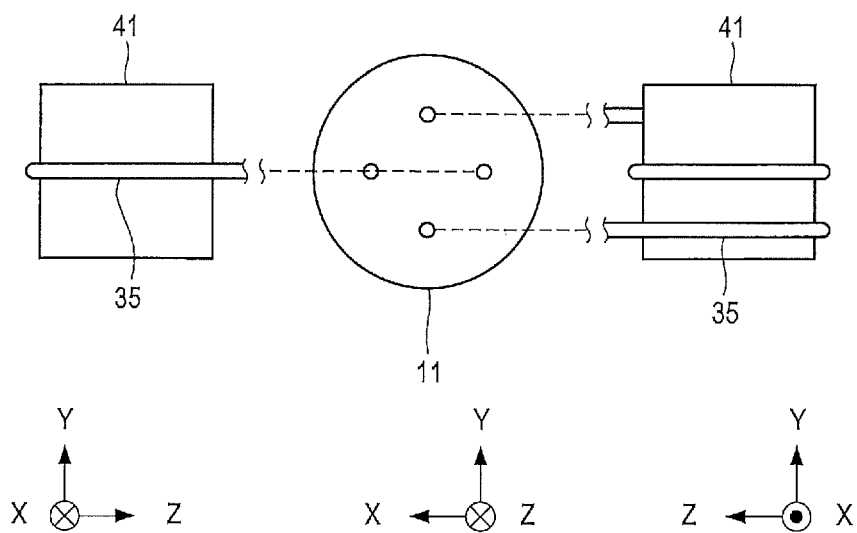
FIG. 6B is a schematic diagram illustrating an arrangement of a wire extending from the pulley to a shaft.

On the other hand, in the case where the wire 35 guided into the shaft 11 is arranged side by side at the same position in the Y-axis direction with a clearance therebetween as shown in FIG. 6B, the wire 35 is wound only in the groove 42 provided in the middle of the pulley 41.

Figure 7A:
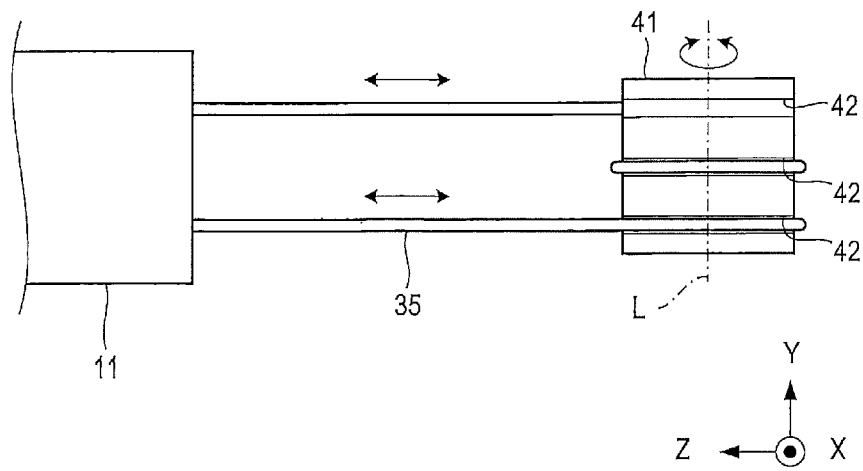
FIG. 7A is a schematic diagram illustrating a movement of the wire in the present embodiment.

When the wire 35 around the pulley 41 shown in FIG. 6A reciprocates with the movement of the drive element 31, the pulley 41 rotates with reciprocating movement of the wire 35 as shown in FIG. 7A. Moreover, the phase of the pulley 41 changes with reciprocating movement of the wire 35. At this time, the wire 35 moves while keeping its positions in the Y-axis direction within a specified range.

In other words, since the wire 35 is wound in the grooves 42 formed along the X-Z plane, it is easy, despite rotation of the pulley 41, to keep the positions in the Y-axis direction where the wire 35 enters the grooves 42 and the positions in the Y-axis direction where of the wire 35 exits the grooves 42 within the specified range. The pulley 41 does not rotate to the positions where the wire 35 enters the grooves 42 and the positions where the wire 35 exits the grooves 42 coincide with the cut-out portions 43.

Figure 7B:
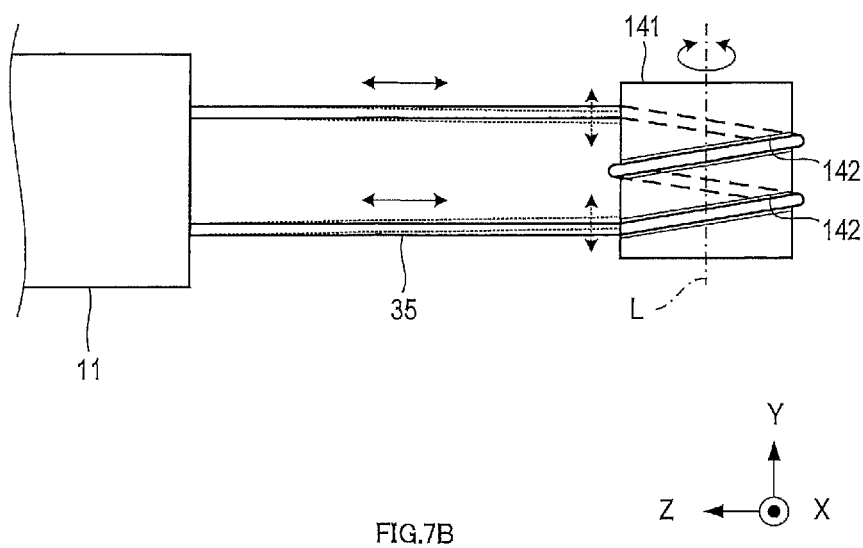
FIG. 7B is a schematic diagram illustrating a movement of the wire in a spiral groove.

In contrast, as shown in FIG. 7B, in the case, for example, where a pulley 141 is provided, on its circumferential surface, with a spiral groove 142 in which the wire 35 is wound, the positions of the wire 35 in the Y-axis direction change with the reciprocating movement of the wire 35. That is, when the pulley 41 rotates with the reciprocating movement of the wire 35, the position where the wire 35 enters the spiral groove 142 and the position where the wire 35 exits move in the Y-axis direction. With this movement, the positions of the wire 35 in the Y-axis direction change.

In the surgical tool 1 configured as described above, the arrangement positions of the pulleys 41 can be changed in an approaching and separating manner in relation to the drive elements 31 and the forceps 12, and thereby adjustment of the tension of the wire 35, that is, tensioning is possible. In comparison with, for example, the tension adjustment method described in Patent Document 1, it is easy to finely adjust the tension and to maintain the adjusted tension. Moreover, it is possible to reduce the variation in tension to stabilize the tension. Thus, the frictional force acting between the drive elements 31 and the forceps 12 is also stabilized. This further facilitates improvement in accuracy of external force estimation as compared with the method in which the frictional force acting between the drive elements 31 and the forceps 12 is unstable.

Increasing the accuracy of the external force estimation in this way enables safer surgery using the surgical tool 1 and surgery with few complications. This furthermore facilitates improvement in QOL of patients and reduction in burden on doctors during surgery, and contributes to improvement on the learning curve of the surgical robot. The term QOL used herein is an abbreviation for quality of life and will be written in the same manner below.

Moreover, the pulleys' rotational shafts 46 and the securing blocks 51 are configured such that the relative positions thereof in the direction of the rotational axis L can be changed. Thus, the rotations of the pulleys 41 are less likely to be inhibited. In the case, for example, where the pulleys' rotational shafts 46 are secured to the first housing portion 21 and the securing blocks 51 are secured to the second housing portion 22, the lengths of the combinations of the pulleys' rotational shafts 46 and the securing blocks 51 are adjusted by changing the relative positions even when the lengths of the combinations are different from the distance between the first and second housing portions 21, 22. Accordingly, the influence of the securing does not easily reach the pulleys 41 supported by the pulleys' rotational shafts 46, and the rotations are less likely to be inhibited.

In the case where three pulleys 41 are provided as in the present embodiment, it is easy to change the arrangement position of each of the three pulleys 41 in the approaching and separating manner. In other words, even after fixing the arrangement position of one pulley 41, the arrangement positions of the other pulleys 41 can be easily changed in the approaching and separating manner.

In the case, for example, where there are no securing blocks 51 and only the pulleys' rotational shafts 46 are provided, in response to the arrangement position of one of the pulleys 41 being fixed, each end of the pulley's rotational shaft 46 of the one pulley 41 comes into contact with the first housing portion 21 or the second housing portion 22. At this time, the first and second housing portions 21, 22 come close to each other and the distance therebetween becomes equal to the length of the pulley's rotational shaft 46. That is, each end of the pulleys' rotational shafts 46 of the other pulleys 41 also comes into contact with the first housing portion 21 or the second housing portion 22. Then, despite an attempt to change the arrangement positions of the other pulleys 41 in the approaching and separating manner, the ends of the pulleys' rotational shafts 46 of the other pulleys 41 cannot be easily moved in the approaching and separating manner since the frictional force acting on the surfaces in contact with the first and second housing portions 21, 22 tends to be large.

In contrast, in the case where the relative positions of the pulleys' rotational shafts 46 and the securing blocks 51 can be changed, the first and second housing portions 21, 22 do not come close to each other even after fixing the arrangement position of one of the pulleys 41. That is, the frictional force acting on the contacting surfaces between the pulleys' rotational shafts 46 of the other pulleys 41 and the first housing portion 21, and the contacting surfaces between the securing blocks 51 and the second housing portion 22 is less likely to be large. Accordingly, even after fixing the arrangement position of one pulley 41, it is easy to change the arrangement positions of the other pulleys 41 in the approaching and separating manner.

Furthermore, the lengths of the combinations are adjusted by changing the relative positions. Thus, a load is less likely to be imposed on the first and second housing portions 21, 22. In the case of the first and second housing portions 21, 22, for example, the load may cause deformation or breakage of the first and second housing portions 21, 22. Even in such a case, it is easy to inhibit deformation and breakage of the first and second housing portions 21, 22 since the load is less likely to be imposed thereon.

Pressing the pulleys' rotational shafts 46 against the first housing portion 21 and pressing the securing blocks 51 against the second housing portion 22 using the elongated holes 23 for pulleys and the securing screws 56 enables fixation of the arrangement positions of the pulleys 41 in relation to at least one of the drive elements 31 and the forceps 12. Increasing the pressing force enables more reliable fixation of the arrangement positions, and reducing the pressing force facilitates changes in the arrangement positions.

Use of the leading ends 49 of the pulleys' rotational shafts 46, extending in the direction of the rotational axis L, and the recesses 52 of the securing blocks 51, engaged with the leading ends 49, allows changes in the positions of the pulleys' rotational shafts 46 relative to the securing blocks 51 in the direction of the rotational axis L. Moreover, it is possible to maintain the relative positions in the direction intersecting the direction of the rotational axis L.

Arrangement of the drive elements 31 between the pulleys 41 and the forceps 12 and transmission of the reciprocating movements of the drive elements 31 to the forceps 12 through the wire 35 wound around the pulleys 41 facilitate adjustment of the tension of the wire 35.

In comparison with the pulley 141 provided with the spiral groove 142, it is easy, despite changes in the phase of the pulley 41, to inhibit changes in the positions of the wire 35 in the Y-axis direction and to stabilize the tension of the wire 35. That is, changes in the positions of the wire 35 in the Y-axis direction are inhibited, and thereby it is easy to inhibit changes in length of the path where the wire 35 is arranged, and to stabilize the tension of the wire 35.

Accordingly, it is also easy to stabilize the frictional force acting between the drive elements 31 and the forceps 12, and to improve the accuracy of the external force estimation as compared with a method in which the frictional force, acting between the drive elements 31 and the forceps 12, is unstable. Improving the accuracy of the external force estimation in this way enables safer surgery with the surgical tool 1 and surgery with few complications. Furthermore, this facilitates improvement in QOL of patients and reduction in burden on doctors during surgery, and contributes to improvement on the learning curve of the surgical robot.

In comparison with the pulley 141 provided with the spiral groove 142, it is easy to inhibit changes, due to the phases of the pulleys 41, in the positions in the Y-axis direction where the wire 35 enters the grooves 42 and the positions in the Y-axis direction where the wire 35 exits the grooves 42. Thus, it requires less attention to the phases of the pulleys 41 when the wire 35 is wound therearound. In other words, it is easier to wind the wire 35 around the pulleys 41.

The technical scope of the present disclosure is not limited to the above embodiment. Moreover, the technical scope of the present disclosure can be modified in various ways without departing from the spirit of the present disclosure. For example, the surgical tool 1 is provided with the forceps 12 in the above embodiment; this, however, should not limit the present invention, and the surgical tool 1 may be provided with other instruments used for surgery.

The invention claimed is:

1. A surgical tool comprising:
   at least one driven portion to which a driving force is transmitted from an external portion;
   a cord-shaped element that transmits a movement of the at least one driven portion to a working portion;
   at least one rotor with a circumferential surface around which the cord-shaped element extending from the at least one driven portion to the working portion is wound;
   a first supporting portion and a second supporting portion arranged such that the at least one rotor is interposed therebetween, the first supporting portion and the second supporting portion supporting the at least one rotor such that the at least one rotor is movable in an approaching and separating manner in relation to at least one of the at least one driven portion and the working portion;
   at least one rotational shaft including a first end securable to the first supporting portion, and supporting the at least one rotor such that the at least one rotor is rotatable about a rotational axis thereof; and
   at least one securing portion arranged between a second end of the at least one rotational shaft and the second supporting portion, a position of the at least one securing portion relative to the at least one rotational shaft being changeable in a rotational axis direction that is a direction of the rotational axis, the at least one securing portion being securable to the second supporting portion.

2. The surgical tool according to claim 1,
   wherein the first supporting portion and the second supporting portion comprise at least one elongated hole extending in an approaching and separating direction of the at least one rotor, and
   wherein at least one stator inserted in the at least one elongated hole is provided to facilitate pressing of the at least one rotational shaft and the at least one securing portion respectively against the first supporting portion and the second supporting portion.

3. The surgical tool according to claim 1,
   wherein one of the at least one rotational shaft and the at least one securing portion comprises a projection extending in the rotational axis direction, and another comprises a recess that engages with the projection.

4. The surgical tool according to claim 1,
   wherein the at least one driven portion is moved linearly in a reciprocating manner by the driving force transmitted,
   wherein the at least one rotor is arranged such that the at least one driven portion is interposed between the at least one rotor and the working portion, and
   wherein, of ends of the cord-shaped element wound around the at least one rotor, a first end of the cord-shaped element is arranged to extend toward the at least one driven portion, and a second end of the cord-shaped element is arranged to extend toward the working portion.

5. The surgical tool according to claim 2,
   wherein one of the at least one rotational shaft and the at least one securing portion comprises a projection extending in the rotational axis direction, and another comprises a recess that engages with the projection.

6. The surgical tool according to claim 2,
   wherein the at least one driven portion is moved linearly in a reciprocating manner by the driving force transmitted,
   wherein the at least one rotor is arranged such that the at least one driven portion is interposed between the at least one rotor and the working portion, and
   wherein, of ends of the cord-shaped element wound around the at least one rotor, a first end of the cord-shaped element is arranged to extend toward the at least one driven portion, and a second end of the cord-shaped element is arranged to extend toward the working portion.

7. The surgical tool according to claim 3,
   wherein the at least one driven portion is moved linearly in a reciprocating manner by the driving force transmitted,
   wherein the at least one rotor is arranged such that the at least one driven portion is interposed between the at least one rotor and the working portion, and
   wherein, of ends of the cord-shaped element wound around the at least one rotor, a first end of the cord-shaped element is arranged to extend toward the at least one driven portion, and a second end of the cord-shaped element is arranged to extend toward the working portion.

8. A surgical tool comprising:
   a housing comprising a first portion and a second portion configured to be coupled together;
   a drive element that is arranged between the first portion and the second portion of the housing and receives a driving force;
   a wire, a portion of which is arranged between the first portion and the second portion of the housing and is connected to the drive element and to a forceps;
   a pulley that is arranged between the first portion and the second portion of the housing to be movable within the housing with respect to at least one of the drive element and the forceps, the pulley comprising a shaft about which the pulley rotates, the shaft having a first end and a second end, the first end being securable to the first portion of the housing; and
   a block that is arranged between the second end of the shaft and the second portion of the housing so that a position of the block is changeable relative to the shaft in an axial direction of the shaft, the block being securable to the second portion of the housing.

9. The surgical tool according to claim 8,
   wherein each of the first portion and the second portion of the housing comprise an elongated hole, and
   wherein a first screw extends through the elongated hole of the first portion of the housing to secure the shaft of the pulley to the first portion of the housing, and a second screw extends through the elongated hole of the second portion of the housing and through the block to secure the shaft of the pulley to the second portion of the housing.

10. The surgical tool according to claim 9,
    wherein one of the shaft and the block comprises a projection extending in the axial direction of the shaft, and the other one of the shaft and the block comprises a recess that is configured to engage with the projection.

11. The surgical tool according to claim 8,
    wherein one of the shaft and the block comprises a projection extending in the axial direction of the shaft, and the other one of the shaft and the block comprises a recess that is configured to engage with the projection.

12. The surgical tool according to claim 8, wherein:
the drive element is moved linearly in a reciprocating manner by the driving force,
the drive element is interposed between the pulley and the forceps, and
wherein a first end of the wire is connected to the drive element and a second end of the wire is connected to the forceps, and a portion of the wire between the first end and the second end is wound around the pulley.

13. The surgical tool according to claim 9, wherein:
the drive element is moved linearly in a reciprocating manner by the driving force,
the drive element is interposed between the pulley and the forceps, and
wherein a first end of the wire is connected to the drive element and a second end of the wire is connected to the forceps, and a portion of the wire between the first end and the second end is wound around the pulley.

14. The surgical tool according to claim 10, wherein:
the drive element is moved linearly in a reciprocating manner by the driving force,
the drive element is interposed between the pulley and the forceps, and
wherein a first end of the wire is connected to the drive element and a second end of the wire is connected to the forceps, and a portion of the wire between the first end and the second end is wound around the pulley.

15. The surgical tool according to claim 11, wherein:
the drive element is moved linearly in a reciprocating manner by the driving force,
the drive element is interposed between the pulley and the forceps, and
wherein a first end of the wire is connected to the drive element and a second end of the wire is connected to the forceps, and a portion of the wire between the first end and the second end is wound around the pulley.

16. A surgical tool comprising:
a housing;
a shaft provided with a forceps on a distal end thereof and connected to one end of the housing at a proximal end thereof; and
wherein the housing comprises:
a drive element that receives a driving force, the driving force being transmitted from the drive element to the forceps via a wire;
a pulley arranged in the housing at an end of the housing opposite from a location at which the shaft is connected to the housing, the pulley being movable within the housing with respect to at least one of the drive element and the forceps, the pulley comprising a pulley shaft about which the pulley rotates that has a first end and a second end, the first end being securable to the housing; and
a block that is arranged between the second end of the pulley shaft and the housing so that a position of the block is changeable relative to the pulley shaft in an axial direction of the shaft, the block being securable to the housing.

17. The surgical tool according to claim 16, further comprising:
a first screw that extends through a first elongated hole in the housing to secure the first end of the pulley shaft to the housing, and
a second screw that extends through a second elongated hole in the housing and through the block to secure the second end of the pulley shaft to the housing.

18. The surgical tool according to claim 17,
wherein one of the pulley shaft and the block comprises a projection extending in the axial direction of the pulley shaft, and the other one of the pulley shaft and the block comprises a recess that is configured to engage with the projection.

19. The surgical tool according to claim 16,
wherein one of the pulley shaft and the block comprises a projection extending in the axial direction of the pulley shaft, and the other one of the pulley shaft and the block comprises a recess that is configured to engage with the projection.

20. The surgical tool according to claim 16, wherein:
the drive element is moved in a reciprocating manner by the driving force,
the drive element is interposed between the pulley and the forceps, and
wherein a first end of the wire is connected to the drive element and a second end of the wire is connected to the forceps, and a portion of the wire between the first end and the second end is wound around the pulley.

* * * * *